US012760082B2

(12) United States Patent
Bao et al.

(10) Patent No.: US 12,760,082 B2
(45) Date of Patent: Oct. 13, 2026

(54) GROWTH HORMONE FUSION PROTEIN AND PREPARATION METHOD AND USE THEREOF

(71) Applicant: JHM BIOPHARMACEUTICAL (HANGZHOU) CO., LTD., Hangzhou (CN)

(72) Inventors: Guoqing Bao, Hangzhou (CN); Liming Guo, Hangzhou (CN); Yubao Shen, Hangzhou (CN); Xin Gao, Hangzhou (CN); Jianan Li, Hangzhou (CN); Chao Wang, Hangzhou (CN); Qi Wu, Hangzhou (CN); Baocai Sun, Hangzhou (CN)

(73) Assignee: JHM BIOPHARMACEUTICAL (HANGZHOU) CO., LTD., Hangzhou (CN)

( * ) Notice: Subject to any disclaimer, the term of this patent is extended or adjusted under 35 U.S.C. 154(b) by 715 days.

(21) Appl. No.: 18/179,012

(22) Filed: Mar. 6, 2023

(65) Prior Publication Data

US 2023/0406901 A1 Dec. 21, 2023

Related U.S. Application Data

(63) Continuation of application No. PCT/CN2022/089962, filed on Apr. 28, 2022.

(30) Foreign Application Priority Data

Dec. 30, 2021 (CN) ......................... 202111658414.X

(51) Int. Cl.
*C07K 14/61* (2006.01)
*A61K 38/00* (2006.01)

(52) U.S. Cl.
CPC .............. *C07K 14/61* (2013.01); *A61K 38/00* (2013.01); *C07K 2319/30* (2013.01)

(58) Field of Classification Search
CPC ................ C07K 14/61; C07K 2319/30; C12R 2001/19; A61P 5/06; C12N 5/70
See application file for complete search history.

(56) References Cited

U.S. PATENT DOCUMENTS 11,186,639 B2 * 11/2021 Harris ................ C07K 16/3069
11,453,711 B2 * 9/2022 Zhang .................... A61K 47/64

FOREIGN PATENT DOCUMENTS

| | | | | |
|---|---|---|---|---|
| CN | 102875683 | A | 1/2013 | |
| CN | 105229035 | A | 1/2016 | |
| CN | 108794634 | A | 11/2018 | |
| CN | 110357969 | A | 10/2019 | |
| CN | 112661858 | A | 4/2021 | |
| EP | 3502143 | A1 | 6/2019 | |
| JP | 2018518553 | A | 7/2018 | |
| JP | 2019533004 | A | 11/2019 | |
| KR | 20020080108 | A | 10/2002 | |
| KR | 20120007182 | A1 | 1/2012 | |
| KR | 1020130079011 | A | 7/2013 | |
| KR | 1020130139342 | A | 12/2013 | |
| KR | 1020170079409 | A | 7/2017 | |
| KR | 1020180135839 | A | 12/2018 | |
| KR | 20190074958 | A | 6/2019 | |
| KR | 20200124176 | A | 11/2020 | |
| WO | WO-2004007687 | A2 * | 1/2004 | ............ C12N 15/66 |
| WO | WO2017055582 | A1 | 4/2017 | |

OTHER PUBLICATIONS

Chen, X. et al., "Fusion protein linkers: Property, design and functionality," Sep. 2012, Advanced Drug Delivery Reviews, 65:1357-1369.

Fatima, A., "The effects of linker length and flexibility of Fc-Fusion Proteins," Nov. 30, 2021, A Thesis in the Field of Biotechnology for the Degree of Masters of Liberal Arts in Extension Studies, Harvard University, 17 pages.

International Search Report and Written Opinion mailed Sep. 28, 2022, in International Application No. PCT/CN2022/089962, 13 pages.

Zhou, L et al., "Single chain Fc-dimer-human growth hormone fuision protein," Nov. 2016, Biomaterials, 117:24-31.

Office Action for Korean Application No. 10-2023-7008758, Dated Jun. 9, 2025, 26 pages.

Fatima, A., "The effects of linker length and flexibility on Fc-Fusion Proteins," Nov. 30, 2021, A Thesis in the Field of Biotechnology for the Degree of Masters of Liberal Arts in Extension Studies, Harvard University, 17 pages.

Zhou, L. et al., "Single chain Fc-dimer-human growth hormone fuision protein for improved drug delivery," Nov. 2016, Biomaterials, 117:24-31.

Office Action dated Feb. 9, 2024 in Chinese Application No. 202111658414.X, 13 pages.

Grant Notice daated Apr. 18, 2024 in Chinese Application No. 202111658414.X, 3 pages.

(Continued)

*Primary Examiner* — Gyan Chandra
(74) *Attorney, Agent, or Firm* — Lee & Hayes, P.C.

(57) ABSTRACT

The present disclosure relates to a growth hormone fusion protein and a preparation method and use thereof. The growth hormone fusion protein includes: a double-stranded structure having a first constant region Fc segment and a second constant region Fc segment; and a growth hormone linked to the first constant region Fc segment, the growth hormone has no methionine at an N-terminus thereof, and the growth hormone fusion protein was expressed by a non-mammalian cell expression system. According to the present disclosure, by adopting the fusion of the growth hormone and the double-stranded structure, the in vivo half-life of the growth hormone can be prolonged, and since each double-stranded structure only carries one growth hormone, the active site of the growth hormone is not affected by steric hindrance, and stronger activity is provided, and since the N-terminus of the growth hormone has no methionine, higher safety is provided.

7 Claims, 1 Drawing Sheet

Specification includes a Sequence Listing.

(56) References Cited

OTHER PUBLICATIONS

Extended European Search Report dated Apr. 12, 2024 in European Application No. 22854765.9, 11 pages.
Officed Action for Japanese Application No. 2023-515840, 9 pages.
Office Action for Korean Appliocation No. 10-2023-7008758, Dtaed Feb. 25, 2026, 14 pages.

* cited by examiner

GROWTH HORMONE FUSION PROTEIN AND PREPARATION METHOD AND USE THEREOF

CROSS-REFERENCE TO RELATED APPLICATIONS

This application is a continuation of International Application No. PCT/CN2022/089962, filed on Apr. 28, 2022, which claims priority to Chinese patent application NO. 202111658414.X, filed on Dec. 30, 2021, the entire disclosures of which are incorporated herein by reference for all purposes.

SEQUENCE LISTING

The Sequence Listing associated with this application is provided in XML format in lieu of a paper copy and is hereby incorporated by reference into the specification. The name of the XML file containing the Sequence Listing is "POI220343PUS_Substitute Sequence listing.XML," created on Apr. 2, 2026, with 14,611 bytes in size, and is being submitted electronically via Patent Center.

FIELD

The present disclosure relates to the field of biotechnology, in particular, to a growth hormone fusion protein and a preparation method and use thereof, and more particularly, to a growth hormone fusion protein, a nucleic acid molecule, an expression vector, a recombinant cell, a method for preparing the growth hormone fusion protein, a pharmaceutical composition, and use of the growth hormone fusion protein, nucleic acid molecule, expression vector, recombinant cell, or pharmaceutical composition in manufacture of medicaments.

BACKGROUND

Human growth hormone (hGH) is a protein hormone secreted by the anterior pituitary of the brain, consists of 191 amino acids and has a molecular weight of 22.1 KDa. The growth hormone can promote bone growth, promote protein synthesis and fat decomposition of the body, increase the number of muscle cells and the volume of muscle cells, regulate the immune system and enhance immunity. The growth hormone can be used for the treatment of conditions such as short stature caused by endogenous growth hormone deficiency in children, Turner syndrome, adult GHD, burns and wound repair, etc., as well as the treatment of short stature caused by chronic renal failure, short bowel syndrome and anti-aging of the elderly.

The long-acting growth hormone available in the market in China mainly has its half-life prolonged through PEGylation to achieve the long-acting purpose. However, it has been reported that the insulin-like growth factor-1 (IGF-1) in children with growth hormone deficiency did not return to a normal level when a PEGylated recombinant human growth hormone was administered to the children. During preclinical animal experiments, it was found that repeated injection of PEGylated protein drugs into experimental animals could cause vacuolar lesions. In addition, as for the conventional hormone expression products, especially the hormone expressed in *Escherichia coli*, due to the presence of the bases ATG at the beginning of the target protein gene, the N-terminus of the expressed protein inevitably contains methionine, and the growth hormone containing no methionine at the N-terminus needs to be realized by means of the fusion signal peptide at the N-terminus of the protein. The presence of N-terminus methionine, especially the N-terminus methionine of the growth hormone, will cause side effects to the treatment.

Therefore, the existing long-acting growth hormone technology still needs to be improved.

SUMMARY

The inventors of the present disclosure fully considers the above problems existing in the related art of growth hormones, and during further researches on recombinant growth hormones, unexpectedly found that some expression systems, such as *Escherichia coli*, can directly express growth hormone containing no methionine at the N-terminus, without the help of the signal peptide.

Therefore, the present disclosure provides a method for efficiently preparing a recombinant growth hormone containing no methionine at an N-terminus thereof.

In a first aspect, the present disclosure provides a growth hormone fusion protein. According to embodiments of the present disclosure, the growth hormone fusion protein includes: a double-stranded structure having a first constant region Fc segment and a second constant region Fc segment; and a growth hormone linked to the first constant region Fc segment of the double-stranded structure. The growth hormone has no methionine at an N-terminus thereof, and the growth hormone fusion protein is expressed by a non-mammalian cell expression system. According to the embodiments of the present disclosure, by fusing the growth hormone and the double-stranded structure, the half-life of the growth hormone in the body can be prolonged; and since each double-stranded structure carries only one growth hormone, the active site of the growth hormone is not affected by steric hindrance, so its activity is stronger, and since the N-terminus of the growth hormone contains no methionine, higher safety is provided.

In a second aspect, the present disclosure provides a nucleic acid molecule. According to embodiments of the present disclosure, the nucleic acid molecule encodes the growth hormone fusion protein in the first aspect. The nucleic acid molecule can be used to effectively express the above-mentioned fusion protein, especially to effectively express monomers of the above-mentioned growth hormone in prokaryotic or lower eukaryotic expression systems, and then form the final growth hormone fusion protein through in-vitro assembly.

In a third aspect, the present disclosure provides an expression vector. According to embodiments of the present disclosure, the expression vector carries the nucleic acid molecule described in the second aspect. The expression vector can be used to effectively express the above-mentioned fusion protein in cells, especially to effectively express monomers of the above-mentioned growth hormone in prokaryotic or lower eukaryotic expression systems, and then form the final growth hormone fusion protein through in-vitro assembly.

In a fourth aspect, the present disclosure provides a recombinant cell. According to embodiments of the present disclosure, the recombinant cell contains: the aforementioned nucleic acid molecule; or the aforementioned expression vector. In a fifth aspect, the present disclosure provides a method for preparing the growth hormone fusion protein of the first aspect, including: obtaining a first monomer and a second monomer of the double-stranded structure, in which the first monomer has the first constant region Fc segment, the second monomer has the second constant region Fc segment, and the growth hormone is linked to the first constant region Fc segment; and forming the first monomer and the second monomer into a heterodimer to obtain the growth hormone fusion protein.

Thus, the aforementioned growth hormone fusion protein can be efficiently produced.

According to some embodiments of the present disclosure, the heterodimer is formed in vitro.

According to some embodiments of the present disclosure, each of the first monomer and the second monomer is expressed in a non-mammalian cell expression system.

According to some embodiments of the present disclosure, the first monomer and the second monomer are expressed in a same non-mammalian cell expression system.

In a sixth aspect, the present disclosure provides a pharmaceutical composition including the growth hormone fusion protein of the first aspect.

In a seventh aspect, the present disclosure provides use of the growth hormone fusion protein, the nucleic acid molecule, the expression vector, the recombinant cell, the growth hormone fusion protein prepared by the aforementioned method for preparing the growth hormone fusion protein, or the pharmaceutical composition in manufacture of a medicament for treating or preventing an abnormal growth hormone-related disease.

In an eight aspect, the present disclosure provides a method for treating or preventing an abnormal growth hormone-related disease in a subject, including: administrating the growth hormone fusion protein, the nucleic acid molecule, the aforementioned expression vector, the recombinant cell, the growth hormone fusion protein prepared by the method for preparing the growth hormone fusion protein, or the pharmaceutical composition to the subject.

In a ninth aspect, the present disclosure provides the growth hormone fusion protein, the nucleic acid molecule, the expression vector, the recombinant cell, the growth hormone fusion protein prepared by the method for preparing the growth hormone fusion protein, or the pharmaceutical composition for use in treating or preventing an abnormal growth hormone-related disease.

According to some embodiments of the present disclosure, the abnormal growth hormone-related disease includes at least one selected from the group consisting of growth hormone deficiency in children, Turner syndrome, short stature caused by chronic renal failure, idiopathic short stature, growth hormone deficiency in adults, short bowel syndrome, and achondroplasia with FGFR3 mutation.

DETAILED DESCRIPTION OF EMBODIMENTS

Figure 1:
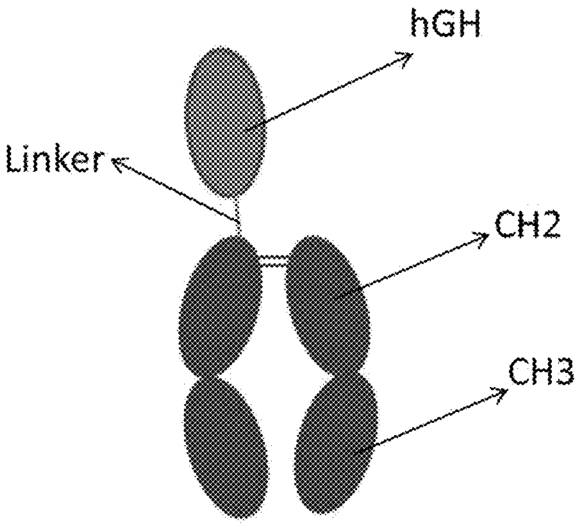
FIG. 1 shows a schematic structural diagram of a fusion protein according to some embodiments of the present disclosure.

The embodiments of the present disclosure will be described in detail below, and the embodiments described below with reference to the accompanying drawings are exemplary, and are intended to explain the present disclosure, but should not be construed as limiting the present disclosure.

In the description of the present disclosure, the relevant terms used herein are explained, and these explanations are only for the convenience of understanding technical solutions, and should not be regarded as a limitation on the claimed solutions of the present disclosure.

Unless otherwise specified, the term "growth hormone" as used herein refers to a human growth hormone or a protein (or referred to as "variant") that has 100% homology or certain homology to the human growth hormone but whose biological functions are not negatively affected. Those skilled in the art can easily obtain the desired site-directed mutation by means of the known amino acid sequence of natural human growth hormone through conventional gene editing means.

Unless otherwise specified, the term "fusion protein" as used herein refers to a novel protein formed by fusing at least two proteins or polypeptides. Usually, the above-mentioned fusion operation can be achieved by techniques such as genetic engineering, for example obtaining an expression product after recombination of two genes through DNA recombinant technology. Here, it means that the growth hormone is fused with an Fc segment of the double-stranded structure. It should be noted that the growth hormone fusion protein does not mean that all parts of the protein are formed by fusion, for example, the two Fc segments in the double-stranded structure can be linked together by chemical bonds such as disulfide bonds.

Unless otherwise specified, the term "identity" as used herein, e.g., the identity between two protein sequences can be determined by conventional methods, e.g., see Current Protocols in Molecular Biology, Chapter 19 (Greene Publishing and Wiley-Interscience, New York), edited by Ausubel et al. (1995); and ALIGN program (Dayhoff (1978), Atlas of Protein Sequence and Structure 5: Suppl. 3 (National Biomedical Research Foundation, Washington, DC). Many methods can be used to align sequences and determine sequence identity, including: Homology comparison algorithm of Needleman et al. (1970), J. Mol. Biol., 48:443; Local homology algorithm, Smith et al. (1981), Adv. Appl. Math., 2:482; Similarity search method, Pearson et al. (1988), Proc. Natl. Acad. Sci., 85:2444; Smith-Waterman algorithm (Meth. Mol. Biol., 70:173-187 (1997)); and BLASTP, BLASTN, and BLASTX algorithm (see Altschul et al. (1990), J. Mol. Biol., 215:403-410). Computer programs utilizing these algorithms are also available and include, but are not limited to: ALIGN or Megalign (DNASTAR) software, or WU-BLAST-2 (Altschul et al., Meth. Enzym., 266:460-480 (1996)); or GAP, BESTFIT, BLAST Altschul et al., FASTA, and TFASTA, available in the Genetics Computing Group (GCG) package, Version 8, Madison, Wisconsin, USA; and CLUSTAL in the PC/Gene program provided by Intelligenetics, Mountain View, California.

Unless otherwise specified, the term "expression vector" as used herein refers to a DNA construct including a DNA sequence operably linked to a suitable regulatory sequence capable of effecting DNA expression in a suitable host. Such a regulatory sequence may include promoters for effecting transcription, optional operator gene sequences for regulating transcription, sequences encoding suitable ribosome-binding sites on mRNA, and sequences for controlling the termination of transcription and translation. Preferably, different expression vectors are used for different cell types. As used herein, "host bacterial strain" or "host cell" refers to a suitable host for an expression vector including the DNA of the present disclosure. As used herein, "non-mammalian cell expression system" refers to systems that employ host cells other than mammalian cells for expression, e.g., microbial cells, such as prokaryotic cells or lower eukaryotic cells.

The present disclosure is completed by the inventors based on in-depth research on the existing growth hormone preparations. Growth hormone deficiency (GHD) in children and adults can be treated with exogenous growth hormone supplementation. At present, commercial recombinant human growth hormones includes common growth hormones and long-acting growth hormones. The common growth hormone has a short half-life in vivo, about 2 to 3 hours, and is quickly cleared by the liver and kidney after injection. Therefore, administration by subcutaneous injection is necessary every day, bringing patients a lot of pain, and at the same time, because of the long-term injection of recombinant human growth hormone in the body, antibodies will be produced in a small number of people, which will affect the efficacy. The long-acting growth hormone overcomes the shortcoming of the short half-life of the common growth hormone in vivo, greatly prolongs the half-life in the body while maintaining high activity, and can be administered by subcutaneous injection every week or longer, which greatly improves the medication compliance of patients.

A recombinant human growth hormone is produced by recombinant DNA technology, and its amino acid sequence is exactly the same as that of a natural human growth hormone, which is a polypeptide strand composed of 191 amino acids, and has two pairs of disulfide bonds formed between positions 53 and 165 and between positions 182 and 189 respectively. There are two receptor binding sites on the surface of the growth hormone molecule, namely binding site 1 and binding site 2. After the growth hormone in the blood circulation reaches the target tissue, it first binds to a growth hormone receptor on the cell membrane and then binds to another growth hormone receptor to form a receptor dimer complex (one growth hormone molecule binds to two growth hormone receptors), activates the downstream JAK2 signaling pathway, and exerts its growth-promoting and other functional effects.

From pituitary-derived human growth hormone to recombinant human growth hormone then to long-acting recombinant human growth hormone, its development has gone through many different stages. The first-generation growth hormone is a pituitary-derived growth hormone extracted from the pituitary, has a limited source and low purity, is susceptible to virus contamination, and has the risk of viral infection after long-term use. The second-generation growth hormone is a recombinant human growth hormone containing 192 amino acids developed by Genentech using *E. coli* inclusion body technology, and has methionine at the N-terminus of the protein, so that it is easy to produce antibodies, and long-term use greatly reduces therapeutic effect of the growth hormone. In addition, since its preparation is in the form of powder injection, it needs to be freeze-dried during the preparation process, which is easy to form aggregates, affecting its growth-promoting effect in vivo.

Growth hormones in recent years are long-acting recombinant human growth hormone water injections prepared by long-acting preparation technologies such as microspheres, hyaluronic acid, and PEG modification. With the long-acting implementation, daily administration is no longer necessary, and weekly administration is possible, which increases patient compliance. The water injection form of the preparation also overcomes the disadvantages of powder injection. However, these preparations have introduced new polymer compounds, and the long-term use of exogenous polymer compounds will cause the production of antibodies in the body, or cause adverse reactions such as immunogenicity, resulting in a decrease in the efficacy of the drug in the body.

The long-acting growth hormone that has been marketed in China mainly prolongs its half-life through PEGylation to achieve the long-acting purpose. However, it has been reported that insulin-like growth factor-1 (IGF-1) did not return to a normal level when PEGylated recombinant human growth hormone was administered to children with growth hormone deficiency. In addition, during preclinical animal experiments, it was found that repeated injection of PEGylated protein drugs into experimental animals could cause fat vacuolar lesions.

Pfizer's Somatrogon is a new molecular entity formed by fusing the C- and N-termini of the native human growth hormone sequence respectively with 2 C-terminus peptides and 1 C-terminus peptide (CTP) derived from the beta subunit of chorionic gonadotropin (HCG) to prolong its half-life and achieve long-acting effect in vivo. Novo Nordisk's Somapacitan is formed by mutating the 101st position leucine of the recombinant human growth hormone to cysteine (L101C), and attaching a fatty acid side chain to the cysteine to achieve the long acting effect in vivo, which introduces synthetic macromolecular products or synthetic fatty acid chains into the body while realizing the long-acting growth hormone by chemical synthetic and/or chemical modification technology, and may have adverse effects on the body after long-term use.

In addition, the inventors found that most of the existing expression systems are mammalian cells, which express glycosylated vectors to realize long-acting growth hormone. Due to the specificity of the action of growth hormone and its receptor, it is necessary to form a growth hormone-receptor dimer complex. In addition, one growth hormone molecule needs to bind two receptor molecules in order to exert its biological effects in vivo normally. Different growth hormone-receptor dimer complex structures affect the degree of in vivo biological effects of the growth hormone and produce steric hindrance of binding the growth hormone to its receptors, resulting in reduced efficacy. Mammalian cells have achieved accessibility for the preparation of Fc fusion proteins or polypeptides, which greatly satisfies the demand for drugs in clinical treatment, but is characterized by complicated preparation processes, long preparation cycles, high preparation costs, difficulty in process amplification, and easy production of glycoform differences and charge isomers. Therefore, the inventors propose microbial expression systems such as prokaryotic expression systems or lower eukaryotic expression systems, e.g., *E. coli*. *E. coli* has the remarkable advantages such as uniform expression products, no glycosylation modification, no glycoform differences and no charge isomers, short fermentation period and low cost, and is especially suitable for the production of recombinant proteins without glycosylation requirements.

Through in-depth researches, the inventors proposed a long-acting growth hormone preparation containing a natural vector with higher purity, better efficacy, fewer adverse reactions, higher safety, easier quality control and lower cost than the existing growth hormones. Further, the structure is designed according to the principle of action of the growth hormone with its receptor, and the *E. coli* expression system is used to produce the long-acting growth hormone to meet the needs of patients for this product. Therefore, a new growth hormone preparation technology can be realized by using a natural carrier to realize the long-acting effect, fully realize genetic engineering expression and significantly reduce the preparation cost. The prepared growth hormone has high purity, high activity (titer), and good efficacy, and compared with other long-acting growth hormones, has significant advantages of high activity and low cost.

Thus, in a first aspect, the present disclosure provides a growth hormone fusion protein. According to some embodiment of the present disclosure, the growth hormone fusion protein includes: a double-stranded structure having a first constant region Fc segment and a second constant region Fc segment; and a growth hormone linked to the first constant region Fc segment of the double-stranded structure. The growth hormone has no methionine at an N-terminus thereof, and the growth hormone fusion protein is expressed by a non-mammalian cell expression system.

According to the embodiments of the present disclosure, by adopting the fusion of the growth hormone with the double-stranded structure, the half-life of the growth hormone in the body can be prolonged; and since each double-stranded structure only carries one molecule of the growth hormone, the active site of the growth hormone is not affected by steric hindrance, so its activity is stronger, and since the N-terminus of the growth hormone has no methionine, it has higher safety.

The double-stranded structure here includes a first monomer and a second monomer, the first monomer has the first constant region Fc segment, the second monomer has the second constant region Fc segment, and the first constant region Fc segment is connected to the growth hormone. Specifically, the first monomer is structured as: hGH-linker-CH2-CH3, the second monomer is structured as: CH2-CH3, and the first monomer is connected to the second monomer by disulfide bonds. In the double-stranded structure provided by the present disclosure, IgG4 Fc is adopted in each constant region Fc segment, and amino acid sequence mutation was carried out on the CH2 and CH3 partial sequences of the natural human IgG4 Fc, and an independently designed rigid Linker sequence is used to form the first monomer and the second monomer. The Fc segments of the double-stranded structure in the present disclosure adopt the CH2 and CH3 partial sequences of the human IgG4 Fc because IgG4 Fc does not cause complement-mediated CDC effect or NK cell-mediated ADCC effect in vivo; and the natural human IgG4 Fc hinge region is not used as the linker, but the independently designed Linker is used instead to avoid the Fab-arm exchange process of IgG4 molecules in vivo and to avoid the IgG4 Fc-caused steric hindrance for the growth hormone.

According to some embodiments of the present disclosure, the growth hormone fusion protein has no glycosylation modification. In this way, the risk of immunogenicity that may be caused by the glycoform difference can be avoided. In addition, because the growth hormone fusion protein has no glycosylation modification, there is no need to consider the quality control difficulties caused by the glycoform difference during preparation, providing more advantages in terms of preparation and quality control.

Glycosylation modification mainly occurs in proteins expressed by mammalian cells. *E. coli* itself has no glycosylation, and therefore expresses proteins having no glycosylation modification. The correctly-glycosylation-modified protein is closer to the natural human protein, but mammalian cells, such as CHO cells (Chinese Hamster Ovary cells for short) are non-mammalian cell lines that express glycoforms different from natural human protein glycoforms and may cause side effects such as immune reactions. Using *E. coli* to express proteins having no glycosylation modification can avoid the possible side reactions caused by glycosylation. The fusion of Fc having no glycosylation modification with the growth hormone can well achieve in vivo long-acting effect of the growth hormone without affecting the activity of the growth hormone, without the need for glycosylation to achieve the above effect.

According to some embodiments of the present disclosure, the non-mammalian cell expression system includes at least one of a prokaryotic expression system or a lower eukaryotic expression system, and preferably the non-mammalian cell expression system includes at least one of an *E. coli* expression system or a yeast expression system. According to some embodiments of the present disclosure, by using at least one of the prokaryotic expression system or the lower eukaryotic expression system, an expression system can be realized with relatively low investment, low culture cost, easy operation, short culture time and high-density fermentation, for example *E. coli* with better quality uniformity and easier control, and the inventors unexpectedly found that at least one of the prokaryotic expression system or the lower eukaryotic expression system does not produce glycosylation of the target protein, avoiding the possible immunogenicity risk due to the glycoform differences as well as the quality control difficulty problem that may be caused by the presence of glycoform differences and charge isomers, and these expression systems use non-animal-derived media and thus are safer.

According to some embodiments of the present disclosure, the growth hormone has one of the following amino acid sequences:

(a) an amino acid sequence shown in SEQ ID NO: 1,

```
SFPTIPLSRLFDNAMLRAHRLHQLAFDTYQEFEEAYIPKEQKYSFLQNP

QTSLCFSESIPTPSNREETQQKSNLELLRISLLLIQSWLEPVQFLRSVF

ANSLVYGASDSNVYDLLKDLEEGIQTLMGRLEDGSPRTGQIFKQTYSKF

DTNSHNDDALLKNYGLLYCFRKDMDKVETFLRIVQCRSVEGSCGF.
```

A wild-type growth hormone contains methionine at an N-terminus thereof, and if it is used for a long time, antibodies will be produced in the body, affecting the therapeutic effect. In order to form a growth hormone having no methionine (M) at the N-terminus, the amino acid $X_1$ (S) is added to the N-terminus, so that after expression, the N-terminus of the protein has no M. If no new amino acid is added to the N-terminus, as shown in the sequence, if the first amino acid of the sequence is F, M will still be present at the N-terminus after expression.

The N-terminus of the amino acid sequence shown in SEQ ID NO: 1 provided by the present disclosure does not contain methionine, which will not cause side effects caused by the N-terminus methionine M. Compared with the natural human growth hormone, the $X_1$ amino acid at the N-terminus does not affect the spatial structure and biological activity of the growth hormone.

According to some embodiments of the present disclosure, the growth hormone fusion protein further includes a linker peptide having one end connected to the growth hormone and another end connected to the double-stranded structure. The linker peptide contains at least one sequence unit GAPQ (SEQ ID NO: 8).

According to some embodiments of the present disclosure, the linker peptide contains 1 to 20, preferably 1 to 5, more preferably 3 sequence units. According to some embodiments of the present disclosure, the C-terminus of the growth hormone is linked to the linker peptide. Compared with conventional linker peptides, the linker peptide according to the embodiments of the present disclosure is a small peptide unit rich in G and/or A and/or P and/or Q and/or K and/or E and/or N amino acids or a unit concatemer of the small peptide units, and such a linker peptide is inflexible and has a more rigid structure, which can avoid interference with the active site of the growth hormone, thereby further improving the biological activity of the finally obtained fusion protein.

The inventors found that when the linker peptide is a flexible linker, such as the usual $(G_mS_n)x$ structure, where m ranges from 1 to 4, n ranges from 0 to 4, and x is an integer between 1 and 20, the structure is highly flexible, and it is easy to "shield" the spatial structures of the two proteins fused with this structure, resulting in steric hindrance and affecting the activity of the target protein. The active site of the growth hormone in the present disclosure exists in the near-C-terminus region. If the Linker is not well designed, the N-terminus of Fc will affect the active site of the near-C-terminus region of the growth hormone, resulting in steric hindrance. As for the linker of a rigid structure, because of its rigidity, the two proteins fused therewith can maintain their own spatial conformations independently and will not produce the phenomenon of spatial "shielding". Therefore, the present disclosure adopts a specific rigid linker, which can avoid the influence of the N-terminus of Fc on the active site of the near-C-terminus region of the growth hormone.

Reasons for interference with growth hormone active site include: a length of the linker; and a structure of the linker. As the length of the linker increases, both the linker itself and Fc may affect the active site of the growth hormone, especially when one of the active sites of the growth hormone in the present disclosure is in the near-C-terminus region, the linker follows the C-terminus, and another fused protein (Fc segment) follows the linker, the spatial structures thereof are close to each other, which may have an interference. The linker cannot be very short, otherwise steric hindrance will be caused. The inventors found that the use of the linker of the above-mentioned length of the present disclosure has no interference with the active site of the growth hormone, and has no effect on the activity of the growth hormone. The inventors also found that if the linker structure is too flexible, and the two fused proteins are prone to "swing" in space, mutually affecting their respective conformations or forming steric hindrance, affecting the binding of the protein to its receptor, and affecting the in-vivo biological function of the protein (the present disclosure forms the hGH/GHR receptor complex, which conducts signal transduction downstream, causing changes in the level of IGF-1 in vivo and promoting growth). Therefore, the present disclosure chooses the rigid linker, so that the spatial positions of the two proteins in front of and behind the linker can be "basically fixed", and the two proteins in front of and behind the linker exist independently in spatial structure, and will not mutually affect the conformations or form steric hindrance, or prevent the binding of the growth hormone to its receptor or the exertion of biological effects in vivo.

According to some embodiments of the present disclosure, the first constant region Fc segment has a different amino acid sequence from the second constant region Fc segment. Thus, formation of homodimers of the fusion protein can be avoided. According to some embodiments of the present disclosure, the first constant region Fc segment and the second constant region Fc segment are adapted to form heterodimers in vitro. According to some embodiments of the present disclosure, the first constant region Fc segment has the following amino acid sequence as set forth in SEQ ID NO: 2:

```
SKYGPPCPPCPAPKAEGGPSVFLFPPKPKDTLMISRTPEVTCVVVDVSQ
EDPEVQFNWYVDGVEVHNAKTKPREEQFNSTYRVVSVLTVLHQDWLNGK
EYKCKVSNKGLPSSIEKTISKAKGQPREPQVYTLPPSQEEMTKNQVSLW
CLVKGFYPSDIAVEWESNGQPENNYKTTPPVLDSDGSFFLYSRLTVDKS
RWQEGNVFSCSVMHEALHNHYTQKSLSLSLGK, and
```

the second constant region Fc segment has the following amino acid sequence as set forth in SEQ ID NO: 7:

```
SKYGPPCPPCPAPEAKGGPSVFLFPPKPKDTLMISRTPEVTCVVVDVSQ
EDPEVQFNWYVDGVEVHNAKTKPREEQFQSTYRVVSVLTVLHQDWLQGK
EYKCKVSNKGLPSSIEKTISKAKGQPREPQVYTLPPSQEEMTKNQVSLS
CAVKGFYPSDIAVEWESQGQPENNYKTTPPVLDSDGSFFLVSRLTVDKS
RWQEGNVFSCSVMHEALHNHYTQKSLSLSLGK.
```

Thus, the efficiency of the fusion protein forming heterodimers in vitro can be further improved, the formation of homodimers can be avoided, the production efficiency can be improved, and the production cost can be reduced.

According to the embodiments of the present disclosure, the present disclosure uses IgG4 Fc as the starting sequence, because IgG4 molecules do not have the complement-mediated CDC effect in vivo or the NK cell-mediated ADCC effect, which avoids the attack to the receptor cells of the growth hormone due to the IgG functional effects. Therefore, higher safety is provided, and the long-acting effect is realized through the Fc.

According to the embodiments of the present disclosure, using IgG4 Fc as the original sequence, the inventors of the present disclosure obtained a variant of Fc through a series of modifications, which was unexpectedly found to effectively avoid the formation of homodimers. After analysis, the inventors found that the charge distribution of the modified Fc segment is conducive to the formation of heterodimers, and the structure is also more stable, which can effectively avoid the formation of multimers during long-term storage of the preparation (more stable), and the three-dimensional structure of the modified Fc segment is also conducive to the formation of heterodimers to achieve stable binding of the first constant region Fc segment and the second constant region Fc segment in the target molecule. In addition, in the modified Fc segment, in order to avoid post-translational modification of the protein, amino acid mutation of the target site was carried out. Post-translational modification (such as deamidation, oxidation, isomerization, etc.) is a common modification after protein expression, and is ubiquitous in protein and polypeptide drugs, seriously affecting the quality of biological products such as proteins, and causing unpredictable clinical adverse reactions of drugs. Among them, deamidation is the most common form of post-translational modification of proteins. In order to avoid the occurrence of post-translational modification of the target molecular protein, especially the occurrence of deamidation, according to the embodiments of the present disclosure, the inventors proved through the HPLC liquid phase diagram that the fusion protein of the present disclosure has no modified body.

According to the embodiments of the present disclosure, the fusion protein of the present disclosure can utilize the natural hGH/GHR mechanism of action to achieve a more effective effect in vivo and a lower administration dose. In the body, the growth hormone binds to its receptor. First, a growth hormone site 1 binds to its receptor to form a growth hormone/receptor complex, and the receptor complex then binds to another growth hormone receptor to form a growth hormone/receptor dimer complex which then activates the downstream JAK2 signaling pathway to promote growth and play other functional roles. The formation of the growth hormone/receptor dimer complex is the key to the exertion of in vivo effects of the growth hormone. The fusion protein according to the embodiments of the present disclosure fully considers the possible steric hindrance effect during the growth hormone-receptor (hGH/GHR) binding process, including the possible steric hindrance of the long-acting vector (Fc), and the steric hindrance that may generated by the growth hormone itself and the linker peptide. According to the embodiments of the present disclosure, the vector molecule, the linker peptide and the effector molecule of the fusion protein structure may all produce steric hindrance effect, which affects the normal play of the effector function of the effector molecule. One of the main factors that can produce steric hindrance is the linker peptide sequence, which is related to the receptor binding region and position of the effector molecule. In order to realize that different molecules (vector and effector molecule) of the fusion protein structure do not affect each other, so as to achieve long-acting effects without affecting the molecular effect (long-acting and efficient), and effectively reduce the steric hindrance between the fused molecules, the receptor binding site of the growth hormone molecule is fully exposed to maximize the biological activity (effect) in vivo while achieving long-acting effects.

According to some embodiments of the present disclosure, the above fusion protein is expressed in non-mammalian cells, e.g. microbial expression systems such as prokaryotic cells or lower eukaryotic cells. As a result, the quality control is easier, with significantly lower production costs. The products expressed in the prokaryotic expression system do not produce glycosylation of the target protein, which avoids the risk of immunogenicity due to the difference in glycoforms, and avoids the quality control difficulty problem that may be caused by the difference in glycoforms and charge isomers. Further, the prokaryotic system culture uses non-animal-derived media, providing higher safety and the well-known advantages of low-cost preparations.

According to the embodiments of the present disclosure, in vitro cell level experiments showed that the in vitro binding activity and biological activity of the highly active recombinant long-acting human growth hormone fusion protein of the present disclosure are significantly higher than those of the long-acting human growth hormone on the market. Animal in-vivo tests showed that the highly active recombinant long-acting human growth hormone fusion protein of the present disclosure has significantly better in-vivo efficacy than the long-acting human growth hormone on the market, and has a good in-vivo PK level. Growth-promoting tests showed that compared with ordinary human growth hormone and the long-acting human growth hormone on the market, the recombinant human growth hormone fusion protein of the present disclosure has a more significant growth-promoting effect. In addition, in-vitro FcRn binding experiments showed that the activity is the same as that of human natural IgG4 Fc, indicating that it may have a longer half-life in vivo, and can be administered once a week or longer, which can greatly reduce the frequency of administration and increase patient compliance. In-vitro cell detection of the binding activity of the highly active recombinant long-acting human growth hormone fusion protein and GHR showed that the two have binding properties that meet the design expectations, indicating that the highly active recombinant long-acting human growth hormone fusion protein has little steric hindrance.

In a second aspect, the present disclosure also provides a nucleic acid molecule. According to some embodiments of the present disclosure, the nucleic acid molecule encodes the growth hormone fusion protein of the first aspect. The nucleic acid molecule can be effectively used to express the above-mentioned fusion protein, especially express monomers of the above-mentioned growth hormone in a prokaryotic or lower eukaryotic expression system, and then the final growth hormone fusion protein is formed through assembly in vitro. It should be noted that the nucleic acid molecule here does not need to encode the entire sequence of the above-mentioned fusion protein, but can include two types of nucleic acid molecules which encode two monomers respectively, and the two monomers can then be assembled in vitro to obtain a heterodimer. For example, the first monomer has a first constant region Fc segment, the second monomer has a second constant region Fc segment, and a growth hormone is linked to the first constant region Fc segment.

In a third aspect, the present disclosure provides an expression vector. According to some embodiments of the present disclosure, the expression vector carries the nucleic acid molecule of the second aspect. The above-mentioned fusion protein can be effectively expressed by using the expression vector in cells, especially monomers of the above-mentioned growth hormone can be effectively expressed in a prokaryotic or lower eukaryotic expression system, and the final growth hormone fusion protein is then formed through in vitro assembly.

In a fourth aspect, the present disclosure provides a recombinant cell. According to some embodiment of the present disclosure, the recombinant cell contains: the aforementioned nucleic acid molecule; or the aforementioned expression vector.

In a fifth aspect, the present disclosure provides a method for preparing the growth hormone fusion protein of the first aspect, including: obtaining a first monomer and a second monomer of the double-stranded structure, the first monomer having a first constant region Fc segment, the second monomer having a second constant region Fc segment, a growth hormone being linked to the first constant region Fc segment; and forming the first monomer and the second monomer into a heterodimer to obtain the growth hormone fusion protein.

As a result, the aforementioned growth hormone fusion protein can be efficiently produced.

According to some embodiments of the present disclosure, non-mammalian cells can be used to express the above-mentioned monomers. As mammalian cell expression systems, CHO cells express the long-acting growth hormone; if the expression product is homodimer, the expressed protein molecules are uniform and have good quality and high purity; however, if the expression product is heterodimer, there will be a great problem that the expression product is not uniform and the purity of the target product is low. The most important impurity is the homodimers respectively formed by the two monomers used to form the heterodimer. Since the target heterodimer is similar in properties to the homodimers of the 2 monomers, it is difficult to remove the homodimers from the expression product. In addition, when using the CHO expression system, the medium composition is complex, the culture cost is high, the risk of virus contamination is high, the culture time is long, the control process is complicated, and the risk of bacterial contamination is high. In addition, compared with the prokaryotic cell reactor, the CHO cell reactor has a huge investment, and a disposable bioreactor has high cost and large investment.

According to some embodiments of the present disclosure, a microbial expression system with relatively low investment, low culture cost, easy operation, short culture time and high-density fermentation can be adopted, such as an *E. coli* expression system (lower cost, better quality uniformity, easier control), which does not use synthetic macromolecular chemicals as long-acting vectors, and does not require in vitro conjugation. Through in vitro assembly, the heterodimer is formed through automatic assembly during the purification of protein, and the inventors unexpectedly found that during the assembly of the heterodimer, there was no formation of homodimers formed respectively by the two monomers used to form the heterodimer during the expression in CHO cells. The in vitro assembly of the first monomer and the second monomer of the present disclosure can be achieved by in vitro assembly methods known in the art, or can be achieved by the methods described in the following specific examples of the present disclosure. After *E. coli* is cultured, expression is induced, cells are disrupted, and inclusion bodies are harvested. After simple purification, the high-purity heterodimer structure target product can be obtained.

In a sixth aspect, the present disclosure provides a pharmaceutical composition including: the growth hormone fusion protein of the first aspect.

According to some embodiments of the present disclosure, the pharmaceutical composition includes the growth hormone fusion protein of the first aspect; and pharmaceutically acceptable excipients.

In a seventh aspect, the present disclosure provides use of the aforementioned growth hormone fusion protein, the nucleic acid molecule, the expression vector, the recombinant cell, the growth hormone fusion protein prepared by the aforementioned method for preparing the fusion protein, and the pharmaceutical composition in manufacture of medicaments for treating or preventing an abnormal growth hormone-related disease.

In an eight aspect, the present disclosure provides a method for treating or preventing an abnormal growth hormone-related disease in a subject, including: administrating the growth hormone fusion protein, the nucleic acid molecule, the aforementioned expression vector, the recombinant cell, the growth hormone fusion protein prepared by the method for preparing the growth hormone fusion protein, or the pharmaceutical composition to the subject.

In a ninth aspect, the present disclosure provides the growth hormone fusion protein, the nucleic acid molecule, the expression vector, the recombinant cell, the growth hormone fusion protein prepared by the method for preparing the growth hormone fusion protein, or the pharmaceutical composition for use in treating or preventing an abnormal growth hormone-related disease.

According to some embodiments of the present disclosure, the abnormal growth hormone-related disease includes at least one selected from the group consisting of growth hormone deficiency in children, Turner syndrome, short stature caused by chronic renal failure, idiopathic short stature, growth hormone deficiency in adults, short bowel syndrome, and achondroplasia with FGFR3 mutation.

In the present disclosure, the terms "rhGH", "growth hormone", "hGH" and "human growth hormone" are used interchangeably, unless otherwise specified.

The solutions of the present disclosure will be explained below in conjunction with the embodiments. Those skilled in the art will understand that the following embodiments are only used to illustrate the present disclosure, and should not be construed as limiting the scope of the present disclosure. If no specific technique or condition is indicated in the embodiments, the technique or condition described in the literature in the field or the product specification is used. The reagents or instruments used without indication of the manufacturer are conventional products that are commercially available.

The specific steps of the present disclosure are described in detail by the following embodiments, but are not limited by the embodiments.

Embodiment 1: Design and Construction of rhGH-Fc/Fc Expression Vector

1.1 Design and Synthesis of Target Genes

The nucleotide sequences of the target genes were designed according to the amino acid sequence of the target protein, and optimized according to the preferred codons of *E. coli*, and the nucleotide sequences were determined as SEQ ID NO: 3 (a first variant) and SEQ ID NO: 4 (a second variant). Synthesis of the designed sequences was entrusted to Bao Bioengineering (Dalian) Co., Ltd.

A nucleotide sequence shown in SEQ ID NO:3:

```
TCTAGAAATAATTTTGTTTAACTTTAAGAAGGAGATATACCATGAGCTTC
CCGACCATCCCGCTGTCTCGTCTGTTCGACAACGCTATGCTGCGTGCTCA
CCGTCTGCACCAGCTGGCGTTCGACACCTACCAGGAATTTGAAGAAGCTT
ACATCCCGAAAGAACAGAAATACTCTTTCCTGCAGAACCCGCAGACCTCT
CTGTGCTTCTCTGAATCTATCCCGACCCCGTCTAACCGTGAAGAAACCCA
GCAGAAATCTAACCTGGAACTGCTGCGTATCTCTCTGCTGCTGATCCAGT
CTTGGCTGGAACCGGTTCAGTTCCTGCGTTCTGTTTTCGCTAACTCTCTG
GTTTACGGTGCTTCTGACTCTAACGTTTACGACCTGCTGAAAGACCTGGA
AGAAGGTATCCAGACCCTGATGGGTCGTCTGGAAGACGGTTCTCCGCGTA
CCGGTCAGATCTTCAAACAGACCTACTCTAAATTCGACACCAACTCTCAC
AACGACGACGCTCTGCTGAAAAACTACGGTCTGCTGTACTGCTTCCGTAA
AGACATGGACAAAGTTGAAACCTTCCTGCGTATCGTTCAGTGCCGTTCTG
TTGAAGGTTCTTGCGGTTTCGGAGCACCTCAGGGTGCTCCACAAGGCGCG
CCGCAAAGCAAATACGGCCCGCCATGTCCACCGTGTCCAGCACCGAAGGC
TGAAGGCGGTCCGTCTGTTTTTCTGTTTCCGCCGAAACCGAAAGACACCC
TGATGATTAGTCGTACCCCGGAAGTTACCTGCGTTGTTGTTGACGTCAGC
CAGGAAGATCCGGAAGTTCAGTTCAACTGGTACGTTGACGGCGTTGAAGT
TCATAACGCGAAAACCAAACCGCGCGAAGAACAGTTCAACAGTACCTATC
GCGTTGTTAGCGTACTGACCGTTCTGCATCAGGATTGGCTGAACGGCAAA
GAGTACAAATGCAAAGTCAGCAACAAAGGCCTGCCGAGCAGCATTGAAAA
```

-continued

```
AACCATCAGCAAAGCGAAAGGCCAACCGCGCGAACCGCAAGTTTATACCC
TGCCGCCGTCTCAGGAAGAAATGACCAAAAACCAGGTCAGCCTGTGGTGT
CTGGTTAAAGGCTTCTACCCGAGCGATATCGCAGTTGAGTGGGAAAGTAA
CGGTCAACCGGAGAACAACTATAAAACCACCCCGCCGGTTCTGGATAGCG
ACGGTAGCTTTTTCCTGTACAGTCGTCTGACCGTTGATAAAAGCCGTTGG
CAGGAAGGCAACGTTTTTAGCTGTAGCGTCATGCACGAAGCCCTGCATAA
CCATTACACCCAGAAAAGCCTGAGCCTGAGTCTGGGTAAATAATAAGGAT
CC
```

A nucleotide sequence shown in SEQ ID NO: 4:

```
TCTAGAAATAATTTTGTTTAACTTTAAGAAGGAGATATACCATGTCTAAA
TACGGCCCGCCATGTCCACCGTGTCCAGCACCGGAGGCTAAAGGTGGTCC
GAGCGTGTTCCTGTTTCCACCGAAACCGAAAGATACCCTGATGATTTCTC
GTACTCCGGAGGTAACTTGCGTAGTAGTTGATGTGAGCCAGGAAGATCCG
GAGGTGCAGTTCAACTGGTATGTTGACGGTGTTGAGGTTCATAACGCCAA
GACTAAACCACGTGAAGAACAGTTCCAAAGCACCTACCGTGTGGTAAGCG
TGCTGACCGTTCTGCACCAAGATTGGCTGCAAGGTAAGGAGTACAAATGT
AAAGTAAGCAACAAAGGCCTGCCGAGCAGCATTGAGAAGACCATCTCTAA
GGCTAAAGGTCAACCACGCGAGCCGCAGGTGTACACTCTGCCACCAAGCC
AGGAAGAGATGACCAAGAATCAGGTGTCTCTGAGTTGTGCAGTTAAGGGT
TTCTACCCGAGCGATATTGCGGTAGAATGGGAATCTCAAGGTCAGCCGGA
GAACAACTATAAGACCACTCCACCAGTTCTGGATTCCGACGGCTCTTTCT
TCCTGGTATCCCGTCTGACCGTTGACAAATCCCGTTGGCAGGAAGGCAAC
GTGTTCTCTTGTTCTGTTATGCACGAGGCGCTGCACAACCACTACACCCA
GAAGTCTCTGTCCCTGAGCCTGGGTAAATAATAAGGATCC
```

The amino acid sequence encoded by SEQ ID NO:3 (the first variant) is shown in SEQ ID NO:5:

```
SFPTIPLSRLFDNAMLRAHRLHQLAFDTYQEFEEAYIPKEQKYSFLQNPQ
TSLCFSESIPTPSNREETQQKSNLELLRISLLLIQSWLEPVQFLRSVFAN
SLVYGASDSNVYDLLKDLEEGIQTLMGRLEDGSPRTGQIFKQTYSKFDTN
SHNDDALLKNYGLLYCFRKDMDKVETFLRIVQCRSVEGSCGFGAPQGAPQ
GAPQSKYGPPCPPCPAPKAEGGPSVFLFPPKPKDTLMISRTPEVTCVVVD
VSQEDPEVQFNWYVDGVEVHNAKTKPREEQFNSTYRVVSVLTVLHQDWLN
GKEYKCKVSNKGLPSSIEKTISKAKGQPREPQVYTLPPSQEEMTKNQVSL
WCLVKGFYPSDIAVEWESNGQPENNYKTTPPVLDSDGSFFLYSRLTVDKS
RWQEGNVFSCSVMHEALHNHYTQKSLSLSLGK
```

The amino acid sequence encoded by SEQ ID NO: 4 (the second variant) is as shown in SEQ ID NO: 6:

```
SKYGPPCPPCPAPEAKGGPSVFLFPPKPKDTLMISRTPEVTCVVVDVSQE
DPEVQFNWYVDGVEVHNAKTKPREEQFQSTYRVVSVLTVLHQDWLQGKEY
```

-continued

```
KCKVSNKGLPSSIEKTISKAKGQPREPQVYTLPPSQEEMTKNQVSLSCAV
KGFYPSDIAVEWESQGQPENNYKTTPPVLDSDGSFFLVSRLTVDKSRWQE
GNVFSCSVMHEALHNHYTQKSLSLSLGK
```

1.2 Construction of Expression Vector

Two ends of the target gene have XbaI and BamHI digestion sites, respectively. The target gene sequence and the pET-28a (+) vector were digested with XbaI and BamHI double enzymes, followed by gel extraction, and the digested target gene fragment was linked to the digested pET-28a (+) long fragment, followed by transformation and screening to obtain genetically engineered bacteria for expressing the target gene.

Embodiment 2: Expression and Purification of rhGH-Fc/Fc Protein

The target genetically engineered bacteria were cultured in a medical bottle containing LB medium. When the OD600 reached 1.6 to 2.0, the bacteria were transferred to a 5 L fermenter for cultivation, with a start culture volume of 2.5 L, a culture temperature at 37° C., and a stirring speed of 6,000 rpm. When the OD600 rose to 50, induction was started with an inducer IPTG at a concentration of 0.5 mM, and the induction duration was 4 to 6 hours.

The bacterial growth condition in the fermentation broth and the expression condition were observed by microscope. The bacteria were collected by centrifugation at 10,000 rpm and 4° C.

The collected bacteria were disrupted by high-pressure homogenization with a disruption pressure of 700 to 800 Bar for at least 2 cycles, until no complete cell exist under the microscopic examination. Inclusion bodies were collected by centrifugation.

In vitro assembly: First, the inclusion body protein of the first variant and the inclusion body protein of the second variant were dissolved respectively in the same inclusion body dissolution buffer containing 8 M urea. After dissolved completely, the two were mixed evenly at a volume ratio of 1:1 to obtain the inclusion body dissolved solution. The evenly mixed inclusion body dissolved solution was added to an assembly buffer at a volume ratio of 1:10 to 1:100, and let stand overnight. The inclusion body dissolution buffer contained the following components: Tris or Tris-HCl, 50 to 100 mM; NaCl, 100 to 150 mM; arginine, 10 to 50 mM; EDTA, 5 to 20 mM; pH 6.0 to 8.0; the above assembly buffer contained the following components: Tris or Tris-HCl, 10 to 20 mM; NaCl, 10 to 50 mM; arginine, 100 to 500 mM; GSSG, 10 to 20 mM; GSH, 0 to 5 mM; EDTA, 5 to 10 mM; Buffer pH 5.0 to 7.0.

Protein purification: The pH of the mixture after standing overnight was adjusted to 3.0 to 3.5 with 1.0 M hydrochloric acid, followed by protein A chromatography, the pH of the eluent was adjusted to 6.0 to 7.0, and hydrophobic chromatography and anion chromatography were conducted respectively to obtain the purified target protein. Conditions of the protein A chromatography: equilibrium buffer: 20 mM $Na_2HPO_4$, 0.15 M NaCl, pH 7.0; elution buffer: 0.1 M glycine, pH 3.0; neutralization buffer: 1 M Tris, pH 8.5. Conditions of the hydrophobic chromatography: equilibrium buffer: 10 to 30 mM Tris or Tris-HCl, 0.5 to 1.0 M NaCl, pH 6.0-7.0, the elution buffer: 10 to 30 mM Tris or Tris-HCl, pH 6.0-7.0. Conditions of the anion chromatography: equilibrium buffer: 10 to 30 mM Tris or Tris-HCl, pH 6.0 to 7.0, the elution buffer: 10 to 30 mM Tris or Tris-HCl, 0.5 to 1.0 M NaCl, pH 6.0 to 7.0.

Embodiment 3: Effects of Rigid Linker and Flexible Linker in rhGH-Fc/Fc Protein on Cell Biological Activity The rigid linker -$(GAPQ)_3$- in SEQ ID NO:5 in Embodiment 1 was replaced with a flexible linker -$(GGGGS)_4$-, and a growth hormone fusion protein (sample name GH$(GGGGS)_4$) containing a flexible linker was obtained according to the same method in Embodiment 2, and was compared with the rhGH-Fc/Fc protein (sample name GH$(GAPQ)_3$) obtained in Embodiment 2 for biological activity.

Biological activity detection process: the cell suspension of BAF3/GHR cells in a logarithmic growth phase in the culture flask was transferred to a 50 ml centrifuge tube with a pipette, and centrifuged at 1,000 rpm for 5 min, with the supernatant discarded. 2 ml of assay culture medium was used to re-suspend the cells to form a single-cell suspension. The single-cell suspension was added to a culture flask containing 15 ml of the assay medium, mixed well, and put into a $CO_2$ incubator for starvation for 24 to 36 hours.

The composition of the assay medium is shown in Table 1 below:

| Name | Theoretical Volume |
|---|---|
| FBS | 10% |
| 100× penicillin-streptomycin-glutamine | 1% |
| 100× nonessential amino acids | 2% |
| 1 mol/L $NaHCO_3$ | 0.2% |
| Hygromycin B | 1 μg/mL |
| RPMI 1640 culture medium | Make up to the prepared volume |

The cell suspension containing the starved BAF3/GHR cells in the culture flask was transferred to a 50 ml centrifuge tube with a pipette, and centrifuged at 1,000 rpm for 5 min, with the supernatant discarded. The cells were re-suspended in 2 ml of the assay medium to prepare a single-cell suspension. 10 μl of the single-cell suspension was put into 10 μl of trypan blue staining solution, and counted with a cell counter or microscope.

The cell density was adjusted to $2.0\pm0.2\times10^5$ cells/ml with the assay medium, and spread 50 μl/well in B to G rows and 2 to 12 columns of a 96-well cell culture plate, 50 μl of the assay medium was added to each well in the first column of B to G rows, and the 96-well cell culture plate was placed into a $CO_2$ incubator for culture for 1 h.

Sample treatment: the test samples (sample GH$(GGGGS)_4$, sample GH$(GAPQ)_3$) were dissolved with sterile water to a concentration of 1 mg/ml. Pre-dilution of the test sample solution: the test sample was diluted with the assay medium to obtain a test sample solution with a concentration of 100 ng/ml, and the dilution factor did not exceed 100 times each time. Test sample: a transparent 96-well plate was used as a dilution plate, and 100 μl of assay medium was added to each well of the dilution plate except the B12 to G12 (positive control) and B2 to G2 wells. 150 μl of 100 ng/ml test sample solution was added to each of the E2 to G2 wells of the dilution plate. 4-fold dilution was conducted on the ELISA plate using a 12-channel micropipette. 50 μL was aspirated from the first column (B2 to G2), transferred to the second column, and mix twenty times. Then 50 μL was transferred from the second column to the third column and mix twenty times. Repeat this step on the entire ELISA plate until reaching the column B10 to G10. 50 L of solution was aspirated from the column B10 to G10 and discarded.

Addition of test sample: after culturing for 1 h in the 96-well cell culture plate, 50 μl was transfer from each well of row B to row G of the dilution plate to the corresponding well of the 96-well culture plate containing cells with a 12-channel micropipette. After transfer, the 96-well cell culture plate was gently shaken for 30 s, and then incubated in a $CO_2$ incubator for 68 to 72 h. After the 96-well cell culture plate was cultured, 10 μl of Alamar-Blue detection solution was added to each drug added well, and the cells were placed in a $CO_2$ incubator for 4 hours. The 96-well plate was placed in a microplate reader, the excitation light was 544 nm, and the emitted light was 590 nm for detection.

The biological activity test results are shown in Table 2 below:

TABLE 2

| Sample name | EC50(nM) | Relative potency |
|---|---|---|
| GH$(GAPQ)_3$ | 1.203 | 100% |
| GH$(GGGGS)_4$ | 3.192 | 37.7% |

The results in Table 2 above show that the rhGH-Fc/Fc protein with the rigid linker of the present disclosure has a smaller EC50 and higher biological activity than the growth hormone fusion protein containing a flexible linker. The inventors found that by using the rigid linker to connect the first monomer and the double-stranded structure, the growth hormone fusion protein provided by the present disclosure maintains its own spatial conformation and does not produce structural "shielding" phenomenon. Use of the rigid linker in the present disclosure can avoid the influence of the N-terminus of Fc on the active site of the near-C-terminus region of the growth hormone, thereby further enhancing the cell biological activity of the growth hormone.

Embodiment 4: Detection of Cell Biological Activity of rhGH-Fc/Fc Protein

The cell biological activity detection of JHM0202 and a marketed control sample (Goldtrophin, a polyethylene glycol recombinant somatropin injection) was carried out with the same method in Embodiment 3. The cell biological activities of the rhGH-Fc/Fc protein and the marketed control sample are shown in Table 3 (EC50: nM).

TABLE 3

| Sample name | EC50 (1st) | EC50 (2nd) | EC50 (3rd) |
|---|---|---|---|
| JHM0202 | 1.316 | 1.113 | 1.110 |
| Marketed control sample (Goldtrophin) | 3.343 | 3.687 | 3.521 |

In Table 3, 1st, 2nd, and 3rd refer to results obtained by three repeating determinations of biological activities.

It can be seen from the above data that the rhGH-Fc/Fc protein sample (JHM0202) purified in Embodiment 2 has a smaller EC50 value (mean ratio 1/2.98) than the marketed control sample. It indicated that JHM0202 protein has better cell biological activity in vitro.

Embodiment 5: Binding Activity of rhGH-Fc/Fc Protein to FcRn rhGH-Fc/Fc protein is a fusion protein of a growth hormone and IgG4 Fc. IgG4 Fc binds to an Fc receptor (FcRn) in a pH-dependent manner, and prolongs the half-life of the growth hormone through a receptor-mediated recycling mechanism. The affinity constant (KD) for binding between the rhGH-Fc/Fc protein and FcRn was detected by SPR technology.

The FcRn sample was treated with a desalting column, the CM5 chip was activated, the rhGH-Fc/Fc protein sample was diluted to 6 μg/mL for injection, the sample was coupled, and the chip was blocked. The analyte FcRn was diluted to 8 concentrations of 46.875, 93.75, 187.5, 375, 750, 1500, 3000 and 6000 nM, injected and detected, with binding time of 60 s and dissociation time of 90 s. The experimental data were fitted by an equilibrium method to obtain kinetic data, and the results are shown in Table 4.

TABLE 4

Binding affinity data of JHM02 sample to human FcRn (pH 6.0)

| Analyte | Ligand | $K_D$ (M) |
|---|---|---|
| FcRn | IgG4 Fc | 2.56E−06 |
| (pH 6.0) | JHM0202 | 2.80E−06 |

The SPR results showed that the rhGH-Fc/Fc sample (JHM0202) and IgG4 Fc had similar binding affinities with human FcRn at pH 6.0, indicating that the rhGH-Fc/Fc protein had a similar in vivo half-life to natural human IgG4 Fc, and can realize the in vivo long-acting effect of rhGH.

Embodiment 6: Detection of In Vivo Growth-Promoting Biological Activity of rhGH-Fc/Fc Protein Young male SD rats were used in the experiment, and the pituitary gland was surgically removed by the ear canal method. The rats were weighed at 2 and 3 weeks after the operation, and the rats with a healthy appearance and a body weight increasing percentage of ±10.0% within 2 to 3 weeks were selected as successfully modeled models. According to a body weight increasing percentage of ±6.0%, 40 models were selected and randomly divided into 4 groups according to the body weight and body weight increasing percentage, respectively a model control group (0 nmol/kg), JHM0202 test sample group (51 nmol/kg, injected once a week), marketed control sample group (Goldtrophin, 51 nmol/kg, injected once a week), and NordiFlex control group (9 nmol/kg) (NordiFlex is a common growth hormone, injected once a day), 10 rats in each group. Additional 10 sham-operated rats were set as normal control group (0 nmol/kg).

Figure 2:
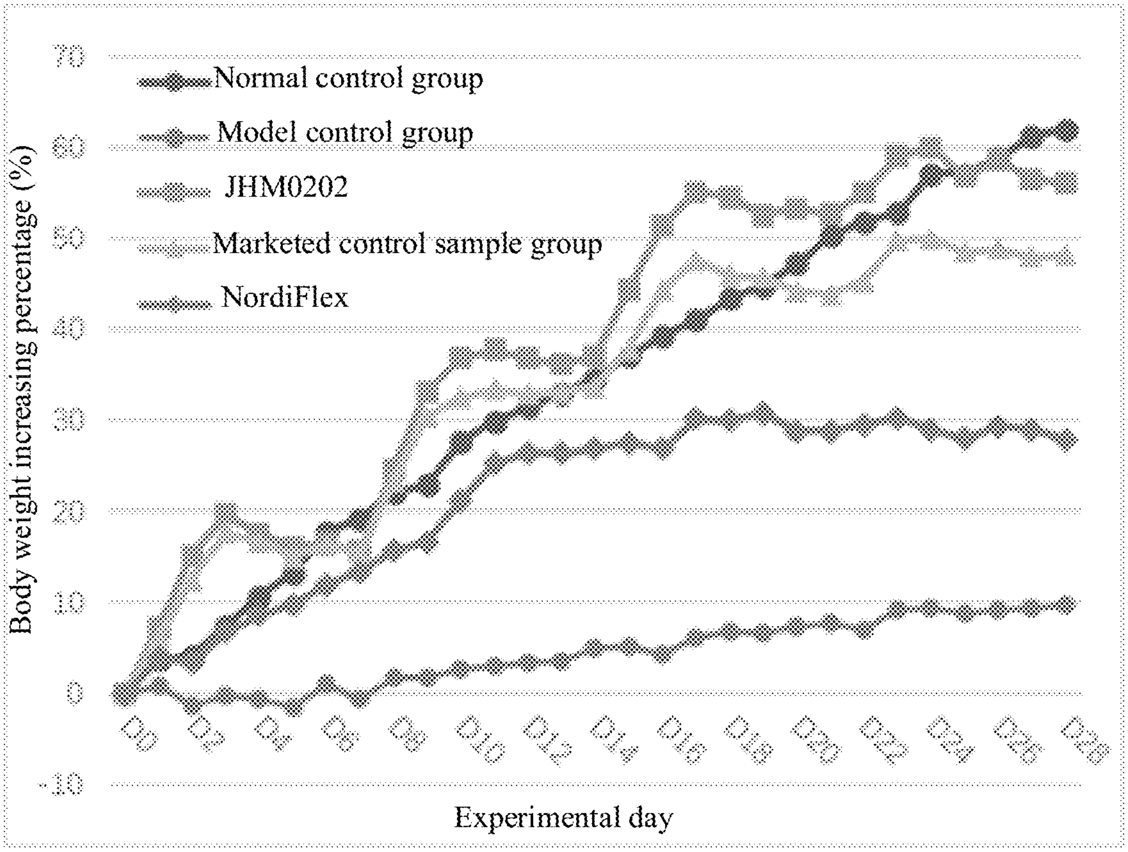
FIG. 2 shows effects of a growth hormone fusion protein of the present disclosure in promoting animal growth in vivo.

After grouping, administration was done through subcutaneous injection. NordiFlex control group was administered once a day for 4 consecutive weeks. The rest of the experimental groups were administered once a week for a total of 4 times. Measurement indicators: the body weight was weighed once a day, and the body weight increasing percentage was calculated. The experimental results are shown in FIG. 2. Based on the data results of the body weight increasing percentage, it can be seen that compared with the model control group, each administration group showed a significant increase in body weight. Both the JHM0202 test sample group and the marketed control sample group achieved a body weight increase comparable to that of the normal rats in the sham-operated control group. Compared with the NordiFlex control group, the body weight increasing percentage of the JHM0202 test sample group on day 28 was significantly greater than that of the NordiFlex control group ($p<0.05$). The body weight increasing percentage of the JHM0202 test sample group on day 28 was higher than that of the marketed control sample group. The above results indicate that the JHM0202 test sample group shows a good in vivo growth-promoting effect.

Embodiment 7: In Vivo Pharmacokinetics of rhGH-Fc/Fc Protein

Pharmacokinetics of the test sample JHM0202 and the marketed control sample (Goldtrophin) in rats were detected. 12 male rats were randomly divided into 2 groups, 6 rats in the test sample JHM0202 group and 6 rats in the marketed control sample group, which was subcutaneously injected with a single injection of 51 nmol/kg of the JHM0202 sample and 51 nmol/kg of the marketed control sample. The sample collection time points of each group were: before administration (0 h) and 2 h, 4 h, 8 h, 12 h, 24 h, 48 h, 72 h, 96 h, 120 h, 168 h, 216 h after administration.

The blood drug concentration in biological samples was detected by ELISA, and the pharmacokinetic parameters were calculated according to the non-compartmental model using WinNonLin8.0 software. The results are shown in Table 5.

TABLE 5

Mean pharmacokinetic parameters of JHM02/Goldtrophin after a single subcutaneous injection in rats (MEAN ± SD)

| PK parameters | JHM0202 Mean ± SD | Marketed control sample Mean ± SD |
|---|---|---|
| $K_{el}$ | 0.0266 ± 0.0062 | 0.0961 ± 0.0040 |
| $T_{1/2}$ | 27.2 ± 6.1 | 7.2 ± 0.3 |
| $t_{max}$ | 22.0 ± 4.9 | 24.0 ± 0.0 |
| $C_{max}$ | 11322 ± 1612 | 9031 ± 921 |
| $AUC_{0-t}$ | 462 ± 113 | 362 ± 22 |
| $AUC_{0-\infty}$ | 463 ± 113 | 362 ± 22 |

After single subcutaneous administration of JHM0202 and the marketed control sample each in a single dose to rats, the blood drug concentrations of the two drugs both showed an increasing first and then decreasing trend, and the peak time ranges were relatively consistent. Compared with the marketed control sample, JHM0202 showed a smaller elimination constant Kel (1/3.6) and a longer elimination half-life $T_{1/2}$ (3.78/1) in vivo, the peak blood drug concentration Cmax of JHM0202 is higher than the marketed control sample (1.25/1), and the in vivo exposure degree $AUC_{0-t}$ of JHM0202 was also higher than that of the marketed control sample (1.28/1). It is revealed that JHM0202 has better in vivo pharmacokinetic properties than the marketed control sample, can achieve a longer in vivo half-life, and has more significant long-acting effect.

Embodiment 8: Effect of rhGH-Fc/Fc Protein on Rat IGF-1 Level

About 1 mL of blood was collected from the orbital venous plexus of rats, the plasma was separated by centrifugation at 3,800 rpm, and the content of IGF-1 was determined by Elisa.

Before administration, on day 3, and on day 24, the rat plasma IGF-1 content in the model control group was significantly lower than that in the normal control group ($p<0.05$). The model control group, the test sample group, the marketed control sample group (Goldtrophin) and the NordiFlex control group (a common growth hormone, injected once a day) had no significant difference in the rat plasma IGF-1 content before administration. Table 6 shows the changes of the rat plasma IGF-1 content in respective experimental groups.

TABLE 6

| Changes in rat plasma IGF-1 content in experimental groups (pg/mL, n = 10, □x ± s) | | | |
|---|---|---|---|
| Group | Before administration | Day 3 | Day 24 |
| Normal control group (0 nmol/kg) | 12198.2 ± 5697.9* | 9814.1 ± 2782.8* | 6002.3 ± 814.7* |
| Model control group (0 nmol/kg) | 65.7 ± 43.7 | 98.3 ± 26.6 | 105.4 ± 48.1 |
| Test sample group (51 nmol/kg) | 42.4 ± 32.1 | 13513.4 ± 10101.8* | 6787.0 ± 9188.9* |
| Marketed control sample group (51 nmol/kg) | 46.2 ± 45.0 | 10556.9 ± 5799.2* | 6155.7 ± 5825.5* |
| NordiFlex control group (9 nmol/kg) | 42.9 ± 43.3 | 495.2 ± 201.6* | 92.3 ± 32.8* |

Note:
*p < 0.05 compared with the model control group;

The analysis results based on IGF-1 showed that: before administration, the rat plasma IGF-1 content in each administration group was significantly lower than that in the normal control group (p<0.05), but there was no significant difference between the administration groups. On day 3, the rat plasma IGF-1 contents in the JHM0202 test sample group and the marketed control group were significantly higher than that of the NordiFlex control group (p<0.05), and the rat plasma IGF-1 content in the JHM0202 test sample group was higher than that in the marketed control sample group, and was greater than that of the normal control group. On day 24, the rat plasma IGF-1 contents in the JHM0202 test sample group and the marketed control sample group were significantly higher than that of the NordiFlex control group (p<0.05), and the rat plasma IGF-1 content in the JHM0202 test sample group was greater than that of the marketed control sample group, and was also greater than that of the normal control group. It indicates that the JHM0202 test sample group has a better in vivo growth-stimulating effect than the marketed control sample group and the NordiFlex control group.

In the description of this specification, description with reference to the terms "one embodiment", "some embodiments", "example", "specific example" or "some examples", etc. mean specific features, structures, materials or characteristics described in connection with the embodiment or example is included in at least one embodiment or example of the present disclosure. In this specification, schematic representations of the above terms are not necessarily directed to the same embodiment or example. Furthermore, the particular features, structures, materials or characteristics described may be combined in any suitable manner in any one or more embodiments or examples. Furthermore, those skilled in the art may combine different embodiments or examples described in this specification, as well as the features of the different embodiments or examples, without conflicting each other.

Although the embodiments of the present disclosure have been shown and described above, it should be understood that the above embodiments are exemplary and should not be construed as limiting the present disclosure. Those skilled in the art may make changes, modifications, substitutions and variations to the embodiments within the scope of the present disclosure.

SEQUENCE LISTING

```
Sequence total quantity: 8
SEQ ID NO: 1          moltype = AA  length = 192
FEATURE               Location/Qualifiers
REGION                1..192
                      note = Amino acid sequence of growth hormone
source                1..192
                      mol_type = protein
                      organism = synthetic construct
SEQUENCE: 1
SFPTIPLSRL FDNAMLRAHR LHQLAFDTYQ EFEEAYIPKE QKYSFLQNPQ TSLCFSESIP  60
TPSNREETQQ KSNLELLRIS LLLIQSWLEP VQFLRSVFAN SLVYGASDSN VYDLLKDLEE  120
GIQTLMGRLE DGSPRTGQIF KQTYSKFDTN SHNDDALLKN YGLLYCFRKD MDKVETFLRI  180
VQCRSVEGSC GF                                                      192

SEQ ID NO: 2          moltype = AA  length = 228
FEATURE               Location/Qualifiers
REGION                1..228
                      note = Amino acid sequence of first constant region FC
                       segment
source                1..228
                      mol_type = protein
                      organism = synthetic construct
SEQUENCE: 2
SKYGPPCPPC PAPKAEGGPS VFLFPPKPKD TLMISRTPEV TCVVVDVSQE DPEVQFNWYV  60
DGVEVHNAKT KPREEQFNST YRVVSVLTVL HQDWLNGKEY KCKVSNKGLP SSIEKTISKA  120
```

```
KGQPREPQVY TLPPSQEEMT KNQVSLWCLV KGFYPSDIAV EWESNGQPEN NYKTTPPVLD  180
SDGSFFLYSR LTVDKSRWQE GNVFSCSVMH EALHNHYTQK SLSLSLGK               228

SEQ ID NO: 3            moltype = DNA  length = 1352
FEATURE                 Location/Qualifiers
misc_feature            1..1352
                        note = Nucleotide sequence of first variant
source                  1..1352
                        mol_type = other DNA
                        organism = synthetic construct
SEQUENCE: 3
tctagaaata attttgttta actttaagaa ggagatatac catgagcttc ccgaccatcc  60
cgctgtctcg tctgttcgac aacgctatgc tgcgtgctca ccgtctgcac cagctggcgt  120
tcgacaccta ccaggaattt gaagaagctt acatcccgaa agaacagaaa tactctttcc  180
tgcagaaccc gcagacctct ctgtgcttct ctgaatctat cccgaccccg tctaaccgtg  240
aagaaaccca gcagaaatct aacctggaac tgctgcgtat ctctctgctg ctgatccagt  300
cttggctgga accggttcag ttcctgcgtt ctgttttcgc taactctctg gtttacggtg  360
cttctgactc taacgtttac gacctgctga aagacctgga agaaggtatc cagaccctga  420
tgggtcgtct ggaagacggt tctccgcgta ccggtcagat cttcaaacag acctactcta  480
aattcgacac caactctcac aacgacgacg ctctgctgaa aaactacggt ctgctgtact  540
gcttccgtaa agacatggac aaagttgaaa ccttcctgcg tatcgttcag tgccgttctg  600
ttgaaggttc ttgcggtttc ggagcacctc agggtgctcc acaaggcgcg ccgcaaagca  660
aatacggccc gccatgtcca ccgtgtccag caccgaaggc tgaaggcggt ccgtctgttt  720
ttctgtttcc gccgaaaccg aaagacaccc tgatgattag tcgtaccccg gaagttacct  780
gcgttgttgt tgacgtcagc caggaagatc cggaagttca gttcaactgg tacgttgacg  840
gcgttgaagt tcataacgcg aaaaccaaac cgcgcgaaga acagttcaac agtacctatc  900
gcgttgttag cgtactgacc gttctgcatc aggattggct gaacggcaaa gagtacaaat  960
gcaaagtcag caacaaaggc ctgccgagca gcattgaaaa aaccatcagc aaagcgaaag  1020
gccaaccgcg cgaaccgcaa gtttataccc tgccgccgtc tcaggaagaa atgaccaaaa  1080
accaggtcag cctgtggtgt ctggttaaag gcttctaccc gagcgatatc gcagttgagt  1140
gggaaagtaa cggtcaaccg gagaacaact ataaaaccac cccgccggtt ctggatagcg  1200
acggtagctt tttcctgtac agtcgtctga ccgttgataa aagccgttgg caggaaggca  1260
acgtttttag ctgtagcgtc atgcacgaag ccctgcataa ccattacacc cagaaaagcc  1320
tgagcctgag tctgggtaaa taataaggat cc                                1352

SEQ ID NO: 4            moltype = DNA  length = 740
FEATURE                 Location/Qualifiers
misc_feature            1..740
                        note = Nucleotide sequence of second variant
source                  1..740
                        mol_type = other DNA
                        organism = synthetic construct
SEQUENCE: 4
tctagaaata attttgttta actttaagaa ggagatatac catgtctaaa tacggcccgc  60
catgtccacc gtgtccagca ccggaggcta aaggtggtcc gagcgtgttc ctgtttccac  120
cgaaaccgaa agataccctg atgatttctc gtactccgga ggtaacttgc gtagtagttg  180
atgtgagcca ggaagatccg gaggtgcagt tcaactggta tgttgacggt gttgaggttc  240
ataacgccaa gactaaacca cgtgaagaac agttccaaag cacctaccgt gtggtaagcg  300
tgctgaccgt tctgcaccaa gattggctgc aaggtaagga gtacaaatgt aaagtaagca  360
acaaaggcct gccgagcagc attgagaaga ccatctctaa ggctaaaggt caaccacgcg  420
agccgcaggt gtacactctg ccaccaagcc aggaagagat gaccaagaat caggtgtctc  480
tgagttgtgc agttaagggt ttctacccga gcgatattgc ggtagaatgg gaatctcaag  540
gtcagccgga gaacaactat aagaccactc caccagttct ggattccgac ggctctttct  600
tcctggtatc ccgtctgacc gttgacaaat cccgttggca ggaaggcaac gtgttctctt  660
gttctgttat gcacgaggcg ctgcacaacc actacaccca gaagtctctg tccctgagcc  720
tgggtaaata ataaggatcc                                              740

SEQ ID NO: 5            moltype = AA  length = 432
FEATURE                 Location/Qualifiers
REGION                  1..432
                        note = Amino acid sequence encoded by first variant
source                  1..432
                        mol_type = protein
                        organism = synthetic construct
SEQUENCE: 5
SFPTIPLSRL FDNAMLRAHR LHQLAFDTYQ EFEEAYIPKE QKYSFLQNPQ TSLCFSESIP  60
TPSNREETQQ KSNLELLRIS LLLIQSWLEP VQFLRSVFAN SLVYGASDSN VYDLLKDLEE  120
GIQTLMGRLE DGSPRTGQIF KQTYSKFDTN SHNDDALLKN YGLLYCFRKD MDKVETFLRI  180
VQCRSVEGSC GFGAPQGAPQ GAPQSKYGPP CPPCPAPKAE GGPSVFLFPP KPKDTLMISR  240
TPEVTCVVVD VSQEDPEVQF NWYVDGVEVH NAKTKPREEQ FNSTYRVVSV LTVLHQDWLN  300
GKEYKCKVSN KGLPSSIEKT ISKAKGQPRE PQVYTLPPSQ EEMTKNQVSL WCLVKGFYPS  360
DIAVEWESNG QPENNYKTTP PVLDSDGSFF LYSRLTVDKS RWQEGNVFSC SVMHEALHNH  420
YTQKSLSLSL GK                                                      432

SEQ ID NO: 6            moltype = AA  length = 228
FEATURE                 Location/Qualifiers
REGION                  1..228
                        note = Amino acid sequence encoded by second variant
source                  1..228
```

-continued

```
                        mol_type = protein
                        organism = synthetic construct
SEQUENCE: 6
SKYGPPCPPC PAPEAKGGPS VFLFPPKPKD TLMISRTPEV TCVVVDVSQE DPEVQFNWYV  60
DGVEVHNAKT KPREEQFQST YRVVSVLTVL HQDWLQGKEY KCKVSNKGLP SSIEKTISKA  120
KGQPREPQVY TLPPSQEEMT KNQVSLSCAV KGFYPSDIAV EWESQGQPEN NYKTTPPVLD  180
SDGSFFLVSR LTVDKSRWQE GNVFSCSVMH EALHNHYTQK SLSLSLGK              228

SEQ ID NO: 7            moltype = AA  length = 228
FEATURE                 Location/Qualifiers
source                  1..228
                        mol_type = protein
                        organism = synthetic construct
REGION                  1..228
                        note = Amino acid sequence of  second constant region FC
                         segment
SEQUENCE: 7
SKYGPPCPPC PAPEAKGGPS VFLFPPKPKD TLMISRTPEV TCVVVDVSQE DPEVQFNWYV  60
DGVEVHNAKT KPREEQFQST YRVVSVLTVL HQDWLQGKEY KCKVSNKGLP SSIEKTISKA  120
KGQPREPQVY TLPPSQEEMT KNQVSLSCAV KGFYPSDIAV EWESQGQPEN NYKTTPPVLD  180
SDGSFFLVSR LTVDKSRWQE GNVFSCSVMH EALHNHYTQK SLSLSLGK              228

SEQ ID NO: 8            moltype = AA  length = 4
FEATURE                 Location/Qualifiers
source                  1..4
                        mol_type = protein
                        organism = synthetic construct
REGION                  1..4
                        note = one sequence unit of linker peptide
SEQUENCE: 8
GAPQ                                                              4
```

What is claimed is:

1. A growth hormone fusion protein, comprising:

a double-stranded structure having a first constant region Fc segment and a second constant region Fc segment;

a growth hormone linked to the first constant region Fc segment of the double-stranded structure; and a linker peptide having one end connected to the growth hormone and another end connected to the double-stranded structure, the linker peptide containing 3 sequence units GAPQ (SEQ ID NO: 8);

wherein the growth hormone has no methionine at a N-terminus thereof;

the growth hormone fusion protein is expressed by a non-mammalian cell expression system;

the growth hormone has the following amino acid sequence as set forth in SEQ ID NO: 1:

SFPTIPLSRLFDNAMLRAHRLHQLAFDTYQEFEEAYIPKEQKYSFLQNP

QTSLCFSESIPTPSNREETQQKSNLELLRISLLLIQSWLEPVQFLRSVF

ANSLVYGASDSNVYDLLKDLEEGIQTLMGRLEDGSPRTGQIFKQTYSKF

DTNSHNDDALLKNYGLLYCFRKDMDKVETFLRIVQCRSVEGSCGF;

the C-terminus of the growth hormone is linked to the linker peptide;

the first constant region Fc segment has a different amino acid sequence from the second constant region Fc segment; the first constant region Fc segment and the second constant region Fc segment are adapted to form a heterodimer in vitro, the first constant region Fc segment has the following amino acid sequence as set forth in SEQ ID NO: 2:

SKYGPPCPPCPAPKAEGGPSVFLFPPKPKDTLMISRTPEVTCVVVDVSQEDPE VQFNWYVD GVEVHNAKTKPREEQFNSTYRVVSVLTVLHQDWLNGKEYKCKVSNKGL PSSIEKTISKAKGQPREPQ VYTLPPSQEEMTKNQVSLWCLVKGFYPSDIAVEWESNGQ PENNYKTTPPVLDSDGSFFLYSRLTVDKSRWQEGNVFSCSVMHEALHNHYTQKSLSLSLGK; and the second constant region Fc segment has the following amino acid sequence as set forth in SEQ ID NO: 7:

SKYGPPCPPCPAPEAKGGPSVFLFPPKPKDTLMISRTPEVTCVVVDVSQ

EDPEVQFNWYVDGVEVHNAKTKPREEQFQSTYRVVSVLTVLHQDWLQGK

EYKCKVSNKGLPSSIEKTISKAKGQPREPQVYTLPPSQEEMTKNQVSLS

CAVKGFYPSDIAVEWESQGQPENNYKTTPPVLDSDGSFFLVSRLTVDKS

RWQEGNVFSCSVMHEALHNHYTQKSLSLSLGK.

2. The growth hormone fusion protein according to claim 1, wherein the growth hormone fusion protein has no glycosylation modification.

3. The growth hormone fusion protein according to claim 1, wherein the non-mammalian cell expression system comprises at least one of a prokaryotic expression system or a lower eukaryotic expression system.

4. The growth hormone fusion protein according to claim 3, wherein the non-mammalian cell expression system comprises at least one of an *Escherichia coli* expression system or a yeast expression system.

5. A pharmaceutical composition, comprising:

the growth hormone fusion protein according to claim 1.

6. A method for treating an abnormal growth hormone-related disease in a subject in need thereof, comprising: administrating the growth hormone fusion protein according to claim 1 to the subject.

7. The method according to claim 6, wherein the abnormal growth hormone-related disease comprises at least one selected from a group consisting of growth hormone deficiency in children, Turner syndrome, short stature caused by chronic renal failure, idiopathic short stature, growth hormone deficiency in adults, short bowel syndrome, and achondroplasia with FGFR3 mutation.

* * * * *